(12) United States Patent
Chen et al.

(10) Patent No.: US 6,899,805 B2
(45) Date of Patent: May 31, 2005

(54) AUTOMATED CHEMICAL MANAGEMENT SYSTEM EXECUTING IMPROVED ELECTROLYTE ANALYSIS METHOD

(75) Inventors: LinLin Chen, Plano, TX (US); Lyndon W. Graham, Hillsboro, OR (US)

(73) Assignee: Semitool, Inc., Kalispell, MT (US)

( * ) Notice: Subject to any disclaimer, the term of this patent is extended or adjusted under 35 U.S.C. 154(b) by 599 days.

(21) Appl. No.: 09/931,268

(22) Filed: Aug. 16, 2001

(65) Prior Publication Data

US 2002/0084195 A1 Jul. 4, 2002

Related U.S. Application Data (63) Continuation-in-part of application No. 09/387,084, filed on Aug. 31, 1999, now Pat. No. 6,365,033, which is a continuation of application No. PCT/US99/09659, filed on May 3, 1999.
(60) Provisional application No. 60/083,882, filed on May 1, 1998.

(51) Int. Cl.[7] .................. G01N 27/416; G01N 27/42
(52) U.S. Cl. ................ 205/794; 205/81; 204/434
(58) Field of Search .................. 205/794, 81, 775; 204/434

(56) References Cited

U.S. PATENT DOCUMENTS

| | | |
|---|---|---|
| 3,649,509 A | 3/1972 | Morawetz et al. |
| 3,878,066 A | 4/1975 | Dettke et al. |
| 3,904,493 A | 9/1975 | Losi et al. |
| 4,055,751 A | 10/1977 | Bussmann et al. |
| 4,090,926 A | 5/1978 | Matson |
| 4,132,605 A | 1/1979 | Tench et al. |
| 4,146,437 A | 3/1979 | O'Keefe |
| 4,229,218 A | 10/1980 | Gulla et al. |
| 4,324,589 A | 4/1982 | Gulla et al. |
| 4,326,940 A | 4/1982 | Eckles et al. |
| 4,541,902 A | 9/1985 | Kinoshita et al. |
| 4,834,842 A | 5/1989 | Langner et al. |
| 4,886,590 A | 12/1989 | Tittle |
| 4,895,739 A | 1/1990 | Bladon |
| 4,917,774 A | 4/1990 | Fisher |

(Continued)

FOREIGN PATENT DOCUMENTS

WO    WO 99/57549 A1    11/1999

OTHER PUBLICATIONS

Z. Sun et al.., *Optimized Bath Control for Void–Free Copper Deposition*. Solid State Technology, pp. 1–10, Nov. 2001.

Dennis Tench and John White. *Cyclic Pulse Voltammetric Stripping Analysis of Acid Copper Plating Baths*, Journal of the Electromechanical Society, vol. 132, No. 4, pp. 831–834. Apr. 1985.

(Continued)

*Primary Examiner*—Alex Noguerola
(74) *Attorney, Agent, or Firm*—Edell, Shapiro & Finnan, LLC (57) ABSTRACT

A method for determining the concentration of an additive X of an electrochemical bath that includes at least one further component Y is set forth. In accordance with the method, a predetermined amount of a starting solution is provided. The starting solution comprises virgin makeup solution that is saturated with the further additive, or forms a mixed solution that is saturated with the further additive when combined with an amount of the electrochemical bath for measurement that is extracted for measurement. A predetermined amount of the extracted electrochemical bath is then added to the predetermined amount of the starting solution to form the mixed solution. At least one electroanalytical measurement cycle it is then executed using the mixed solution and the results of the measurement cycle are compared with a known measurement standard.

26 Claims, 4 Drawing Sheets

U.S. PATENT DOCUMENTS

| | | | |
|---|---|---|---|
| 4,917,777 | A | 4/1990 | Fisher |
| 4,948,473 | A | 8/1990 | Phillippi |
| 4,952,286 | A | 8/1990 | Bladon et al. |
| 5,007,990 | A | 4/1991 | Bladon |
| 5,192,403 | A | 3/1993 | Chang et al. |
| 5,196,096 | A | 3/1993 | Chang et al. |
| 5,223,118 | A | 6/1993 | Sonnenberg et al. |
| 5,234,573 | A | 8/1993 | Takami |
| 5,364,510 | A | 11/1994 | Carpio |
| 5,368,715 | A | 11/1994 | Hurley et al. |
| 5,372,293 | A | 12/1994 | Corlay et al. |
| 5,389,215 | A | 2/1995 | Horiuchi et al. |
| 5,391,271 | A | 2/1995 | Ludwig |
| 5,484,626 | A | 1/1996 | Storjohann et al. |
| 5,509,772 | A | 4/1996 | Doche |
| 5,534,128 | A | 7/1996 | Aso et al. |
| 6,113,769 | A | 9/2000 | Uzoh et al. |
| 6,254,760 | B1 | 7/2001 | Shen et al. |
| 6,280,602 | B1 | 8/2001 | Robertson |
| 6,288,561 | B1 | 9/2001 | Leedy |
| 6,318,951 | B1 | 11/2001 | Schmidt et al. |
| 6,365,033 | B1 | 4/2002 | Graham et al. |
| 6,471,845 | B1 | 10/2002 | Dukovic et al. |
| 6,551,479 | B1 | 4/2003 | Graham et al. |

OTHER PUBLICATIONS

Hobart H. Willard, et al., *Instrumental Methods of Analysis*. Fifth Edition. D. Van Nostrand Company, New York, N.Y.. pp. 647–656. 1974.

Frederick A. Lowenheim. *Electroplating*. McGraw–Hill Book Company, pp. 120 & 121. 1979.

AUTOMATED CHEMICAL MANAGEMENT SYSTEM EXECUTING IMPROVED ELECTROLYTE ANALYSIS METHOD

CROSS-REFERENCE TO RELATED APPLICATIONS

This application is a continuation-in-part of U.S. patent application Ser. No. 09/387,084, filed Aug. 31, 1999, titled "Methods and Apparatus for Controlling and/or Measuring Additive Concentration in an Electroplating Bath" (now issued as U.S. Pat. No. 6,356,033), which is a continuation of PCT/US99/09659, filed May 03, 1999 and published in English under PCT Article 21(2), titled "Methods and Apparatus for Controlling and/or Measuring Additive Concentration in an Electroplating Bath", which claims priority from U.S. Provisional Patent Application Ser. No. 60/083,882, filed May 1, 1998, entitled "Closed Loop Electrolyte Composition Monitoring and Control System for Copper Interconnect Applications". The disclosures of these applications are incorporated herein by reference in their entireties.

STATEMENT REGARDING FEDERALLY SPONSORED RESEARCH OR DEVELOPMENT

Not Applicable

BACKGROUND OF THE INVENTION

One technology that is rapidly coming to the forefront for the formation of microelectronic devices and components is electrochemical deposition, which includes both electroplating and electroless plating of metal to form microelectronic features on a microelectronic workpiece. Though electrochemical deposition has long been employed as a fundamental step in fabrication of multilevel printed circuit boards, application of electrochemical deposition to fill sub-micron interconnect features is relatively recent and poses further additional problems, including the need for more stringent control of the electrolyte bath composition.

Electrochemical deposition is a complex process involving multiple ingredients in the electrolytic bath. If the electrolytic bath is to provide high-quality deposited films (blanket or patterned) on the surface of the substrate, the concentration of several of the constituents of the bath should be maintained. As such, the ability to monitor and control the composition of the bath is one of the important factors in ensuring uniform and reproducible film properties. In semiconductor and microelectronic component applications, the electronic and morphological properties of the metal films are of principal importance in determining final device performance and reliability. The stability of later microfabrication processes in the manufacturing sequence likewise frequently depends on repeatable mechanical properties, including modulus, ductility, hardness, and surface texture of the deposited material. All of these deposit properties are controlled or strongly influenced by the composition of the electrolytic bath.

Measurement and control of proprietary organic compounds that serve to modify the deposit properties through adsorption onto and desorption from the cathode surface during, for example, electroplating, are important since they affect the diffusion rate of metal cations to nucleation and growth sites. These compounds are typically delivered as multi-component packages from chemistry vendors. One of the functions of the additive packages is to influence the throwing power of the electroplating bath: the relative insensitivity of plating rate to variations in cathodic current density across the wafer or in the vicinity of surface irregularities. The throwing power of the electrolyte has an effect on the cross-wafer uniformity of deposited film thickness and the success with which ultrafine trenches and vias (holes) are filled without included seams or voids. Organic additives have also been shown to have substantial effects on mechanical film properties. Detection and quantification of these bath constituents is complicated by the fact that they are effective at very low concentrations in the electrolyte, for example, at several ppm or less.

Bath analysis for microelectronic applications is strongly driven by the need to limit variability and maintain device yields through maintenance of optimized process parameters. One method for controlling such ingredients in an electroplating bath is to make regular additions of particular ingredients based upon empirical rules established by experience. However, depletion of particular ingredients is not always constant with time or use. Consequently, the concentration of the ingredients is not actually known and the level in the bath eventually diminishes or increases to a level where it is out of the acceptable concentration range. If the additive content concentration deviates too far from the target value, the quality of the deposit suffers and the deposit may be dull in appearance and/or brittle or powdery in structure. Other possible consequences include low throwing power and/or plating folds with bad leveling. Accordingly, further evaluation techniques may be used instead of or in an addition to the more conventional empirical techniques.

One method for evaluating the quality of an electroplating bath is disclosed in Tench U.S. Pat. No. 4,132,605 (hereafter the Tench patent). In accordance with the procedures of the Tench patent, FIG. 1 of which is illustrated here, the potential of a working electrode 10 is swept through a voltammetric cycle, including a metal plating range and a metal stripping range, for at least two baths of known plating quality and an additional bath whose quality or concentration of brightener is to be evaluated. The integrated or peak current utilized during the metal stripping range is correlated with the quality of the bath of known quality. The integrated or peak current utilized to strip the metal in the bath of unknown quality is compared to the correlation and its quality evaluated. In a preferred embodiment of said patent, the potential of an inert working electrode 10 is swept by a function generator through the voltammetric cycle. An auxiliary electrode 20 immersed in the plating bath is coupled in series with a function generator and a coulometer to measure the charge from the working electrode 10 during the stripping portion of the cycle.

An improvement to the method disclosed in the Tench patent is described by Tench and White, in the *J. Electrochem. Soc.*, "Electrochemical Science and Technology", April, 1985, pp. 831–834 (hereafter the Tench publication). In accordance with the Tench publication, contaminant buildup in a copper plating bath affects the copper deposition rate, and thus interferes with brightener analysis. The Tench publication teaches a technique that involves sequentially pulsing the electrode between appropriate metal plating, metal stripping, cleaning, and equilibrium potentials whereby the electrode surface is maintained in a clean and reproducible state. The method set forth in that publication is in contrast to the continuous sweep cycle utilized in the above-referenced patent. Stated otherwise, whereas the process of the Tench patent involves a continuous voltammetric sweep between about −600 mV and +1,000 mV versus a working electrode and back over a period of about 1 minute, the Tench publication pulses the potential, for example at −250 mV for 2 seconds to plate, +200 mV for a time sufficient to strip, +1,600 mV to clean for several seconds, +425 mV for 5 seconds to equilibrate, all potentials referenced to a saturated Calomel electrode. After the foregoing, the cycle is repeated until the difference between successive results are within a predetermined value range, for example, within 2% of one another.

Although the procedure of the Tench publication provides some improvement over the procedure of the Tench patent, the present inventor has recognized several areas that need improvement. For example, neither of the foregoing methods suitably address the measurement of individual constituents of electrochemical baths having two or more constituents.

BRIEF SUMMARY OF THE INVENTION

A method for determining the concentration of an additive X of an electrochemical bath that includes at least one further component Y is set forth. In accordance with the method, a predetermined amount of a starting solution is provided. The starting solution comprises virgin makeup solution that is saturated with the further additive, or forms a mixed solution that is saturated with the further additive when combined with an amount of the electrochemical bath for measurement that is extracted for measurement. A predetermined amount of the extracted electrochemical bath is then added to the predetermined amount of the starting solution to form the mixed solution. At least one electroanalytical measurement cycle it is then executed using the mixed solution and the results of the measurement cycle are compared with a known measurement standard.

The teachings associated with the foregoing method may be used to implement a corresponding method in an automatic analysis and dosing system. More particularly, a method for determining the amount of an electrochemical bath additive that is to be automatically added to an electrochemical bath by the dosing system is also set forth. In accordance with this method, the amount of the electrochemical bath additive that is to be added it is dependent on a measurable value related to an amount of a component X in the electrochemical bath that is to be measured. As above, the electrochemical bath also includes at least one further component Y. The automatic analysis and dosing system is programmed to provide a predetermined amount of a starting solution that is comprised of virgin makeup solution that is saturated (or otherwise—see above) with the further component Y. An amount of the electrochemical bath is then automatically extracted for measurement and a predetermined amount of the extracted electrochemical bath is automatically added to the predetermined amount of the starting solution to form a mixed solution that is substantially saturated with the further component Y. At least one electroanalytical measurement cycle is then executed using the mixed solution and the results of the electroanalytical measurement cycle are used to determine the amount of additive that is to be dispensed by the dosing system.

DETAILED DESCRIPTION OF ONE OR MORE EMBODIMENTS OF THE INVENTION

In order to comprehend the context of the present invention, an understanding of the various techniques suitable for analyzing an electroplating bath is helpful. To this end, a description of certain bath analysis techniques are set forth.

A major category of analysis suitable for monitoring an electroplating bath is electroanalysis. Electroanalytical methods use electrically conductive probes, called electrodes, to make electrical contact with an electrochemical bath that is to be analyzed. Such electrochemical baths are used, for example, to electroplate a metal or the like onto the surface of a microelectronic workpiece. The electrodes are used in conjunction with electronic devices to which they are attached to provide electrical energy to a sample extracted from the bath and measure a corresponding electrical parameter response of the sample to the electrical energy. The measured parameter, in turn, is indicative of the type and/or quantity of additives in the electrochemical bath.

Faradaic electroanalysis is attractive as an investigative analytical method principally because what is studied is the electrochemical activity of the bath sample under applied electrical stimulus; the measured responses are related in a fundamental way to the properties that influence the quality of the metal deposition process itself. Electroanalysis further offers the opportunity to study the mechanisms and kinetics of the plating process, and the influences that various electrochemical bath components exert on plating rate suppression and acceleration.

Generally stated, electroanalytical methods are divided into categories according to the electrical parameters that are measured. The major electroanalytical methods include potentiometry, amperometry, conductometry, voltammetry (and polarography), and coulometry. The names of the methods reflect the measured electrical property or its units. Potentiometry measures electrical potential (or voltage) while maintaining a constant (normally nearly zero) electrical current between the electrodes. Amperometry monitors electrical current (amperes). Conductometry measures conductance (the ability of a solution to carry an electrical current). Coulometry is a method that monitors the quantity of electrical charge (coulombs) that is consumed during an electrochemical reaction involving the analyte.

Voltammetry is a technique in which the potential is varied in a regular manner while the current is monitored. Voltammetry (or amperometry) involves the investigation of the current that develops in an electrochemical cell as a consequence of applied potential between a working and auxiliary electrode pair, with the potential measured against a suitable reference electrode.

Figure 1:
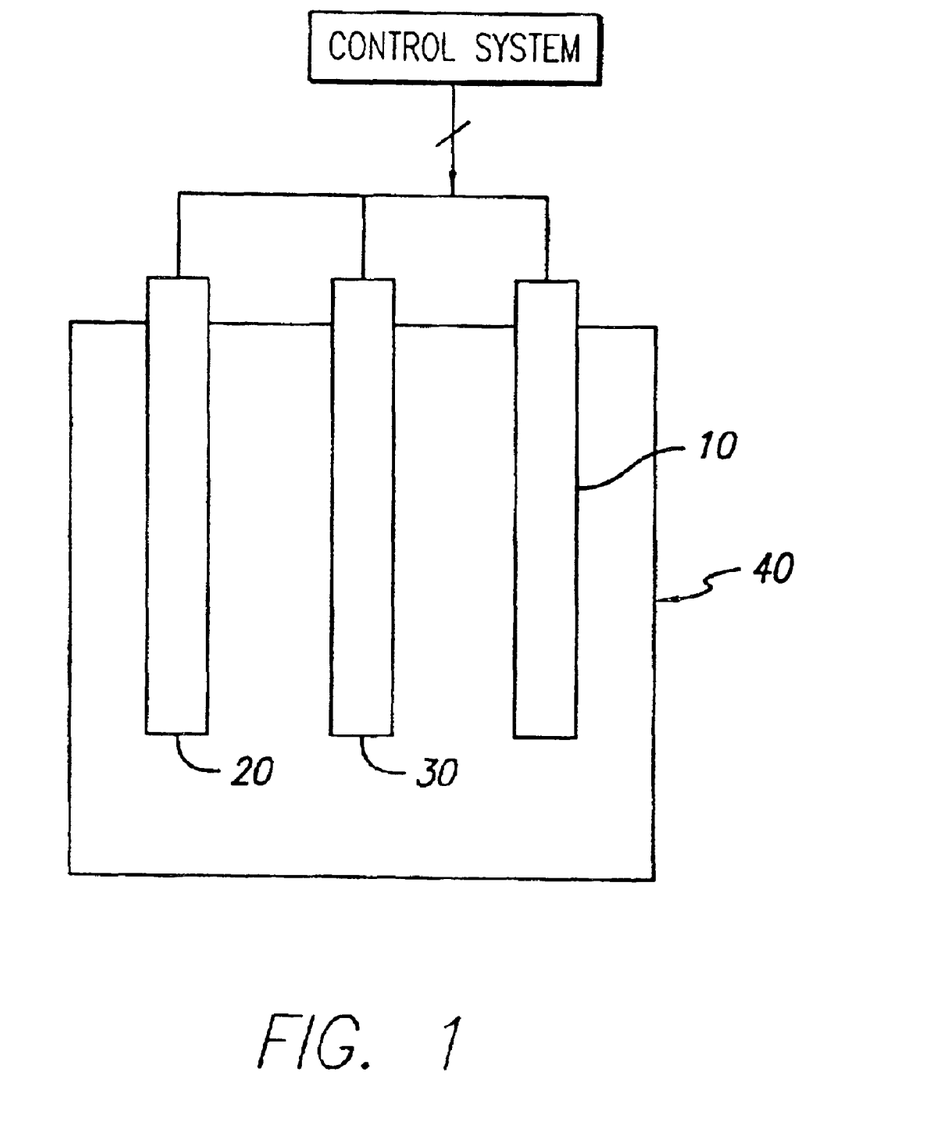
FIG. 1 is an illustration of the basic components of an electrochemical cell that maybe used to implement one or more of the disclosed electroanalytical methods in accordance with the teachings of the present invention.

FIG. 1 is a schematic diagram of a basic electroanalytical cell. In the basic cell, three electrodes are immersed in a container 40: a working electrode 10, an auxiliary electrode 20, and a reference electrode 30. The reference electrode 30 may, for example, be a Ag/AgCl double junction or Saturated Calomel Electrode (SCE). The working electrode 10, for example, may be one of several types, including a drop mercury electrode (DME), a hanging mercury drop electrode (HMDE), a mercury thin film electrodes (MTFE), or an inert electrode which may be either stationary or of a rotating electrode configuration (e.g., RRDE, RCE, RDE). While the mercury-based electrodes offer the advantage of a surface that can be periodically 'renewed' to offer immunity to drift in electrochemical responses associated with changes in surface conditions (e.g., deposit build-up or smutting), inert RDE-type working electrodes with Pt, Pd, Ir, or Rh surfaces are most often employed in systems dedicated to plating bath analysis for convenience of system set-up, maintenance, and waste handling. The apparatus of FIG. 1 employs an RDE-type electrode in which relative motion between the working electrode 10 and the bath is established by a motor (not illustrated) that rotates the working electrode 10. Electrical contact to the working electrode 10 is made by, for example, slip brushes or the like. Neither the processes nor the apparatus of the present invention are limited to a particular electrode type or electroanalytical cell configuration.

A computer or similar control system maybe used to control an electronic potentiostat that, in turn, controls the energy input to the working electrode 10 and the reference electrode 30. Using a suitable program, one or more energy input sequences may be applied to the electroanalytical cell to obtain measurement that are used in determining the amount of a target constituent, such as a bath additive.

One of the difficulties encountered when trying to determine the amount of a constituent in an electrochemical bath is the fact that most electrochemical baths include a variety of different constituents. Many of these constituents are additives that are proprietary to the particular company providing the electrochemical bath. These constituents/additives generally have different effects on the electrochemical deposition process. For example, some additives enhance electroplating while others act as electroplating suppressors that inhibit electroplating. It is therefore difficult to execute some electroanalysis techniques that rely on the plating and/or stripping of a metal onto or from an electrode in determining the amount of a particular additive, such as an enhancer or suppressor in the electroplating bath.

Figure 2:
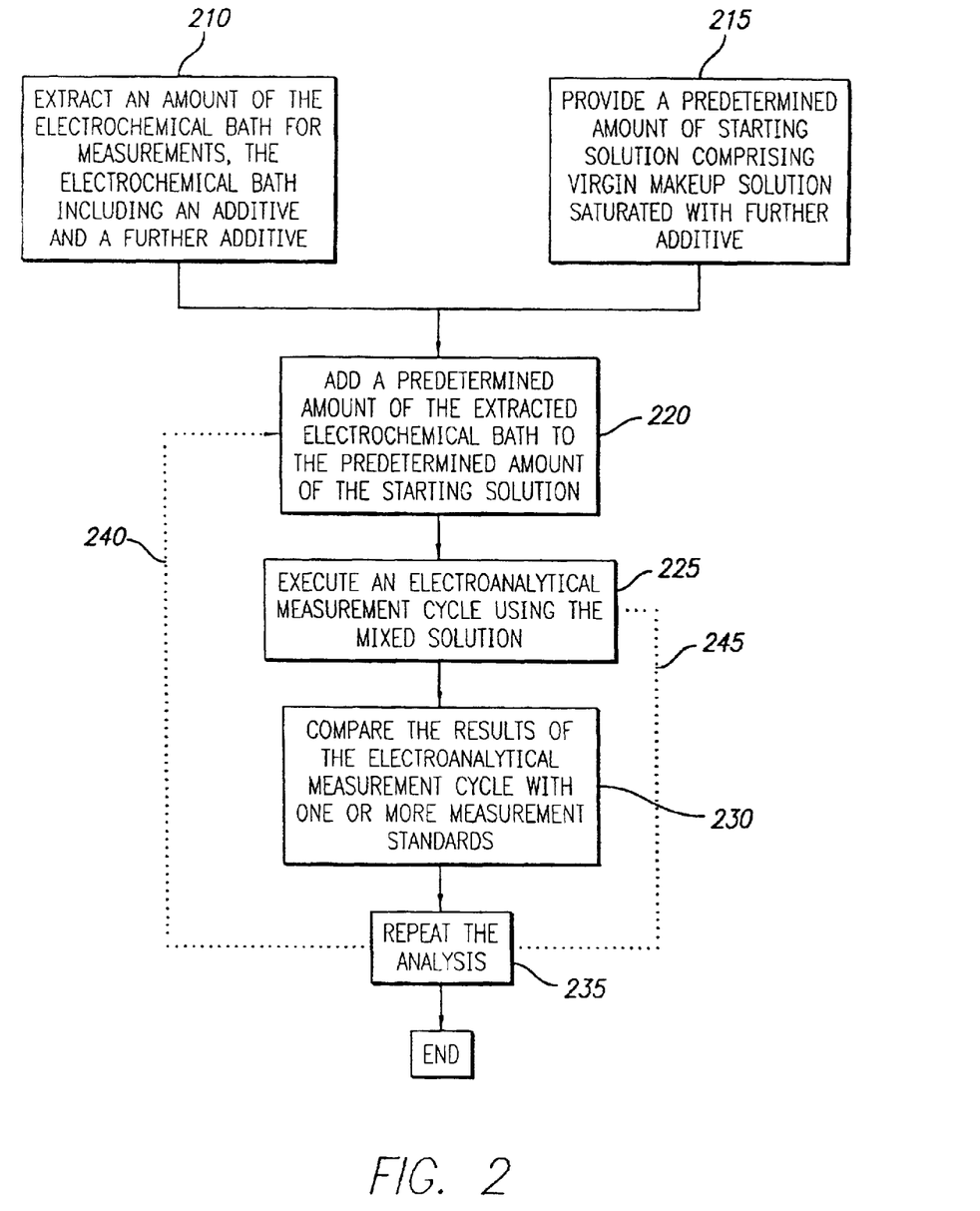
FIG. 2 is a flowchart illustrating a process sequence used to analyze an electrolytic bath in accordance with one embodiment of the present invention.

FIG. 2 is a flowchart illustrating one embodiment of a method that may be used to determine the concentration of a target constituent/additive (these terms are used synonymously herein). As illustrated at step 210, an amount of the electrochemical bath is extracted from, for example, an apparatus that is using the bath to deposit a material onto the surface of a microelectronic workpiece. The electrochemical bath is comprised of at least two additives/constituents: X and Y. The concentration, or other measurable quantity, of at least one of the additives of the electrochemical bath is to be measured. For purposes of the following description, it will be assumed that additive/constituent X is the target constituent that is to be measured. As will be set forth below, the quantity of X that is measured can be used to determine the proper amount of X and/or other bath additives that are to be added to the electrochemical bath by a corresponding dosing system.

In another step, shown here as step 215, a predetermined amount of a starting solution is provided. Steps 210 and 215 may be executed serially, in no particular order, or concurrently. It is for this reason that they are shown here as separate parallel operations.

Figure 3:
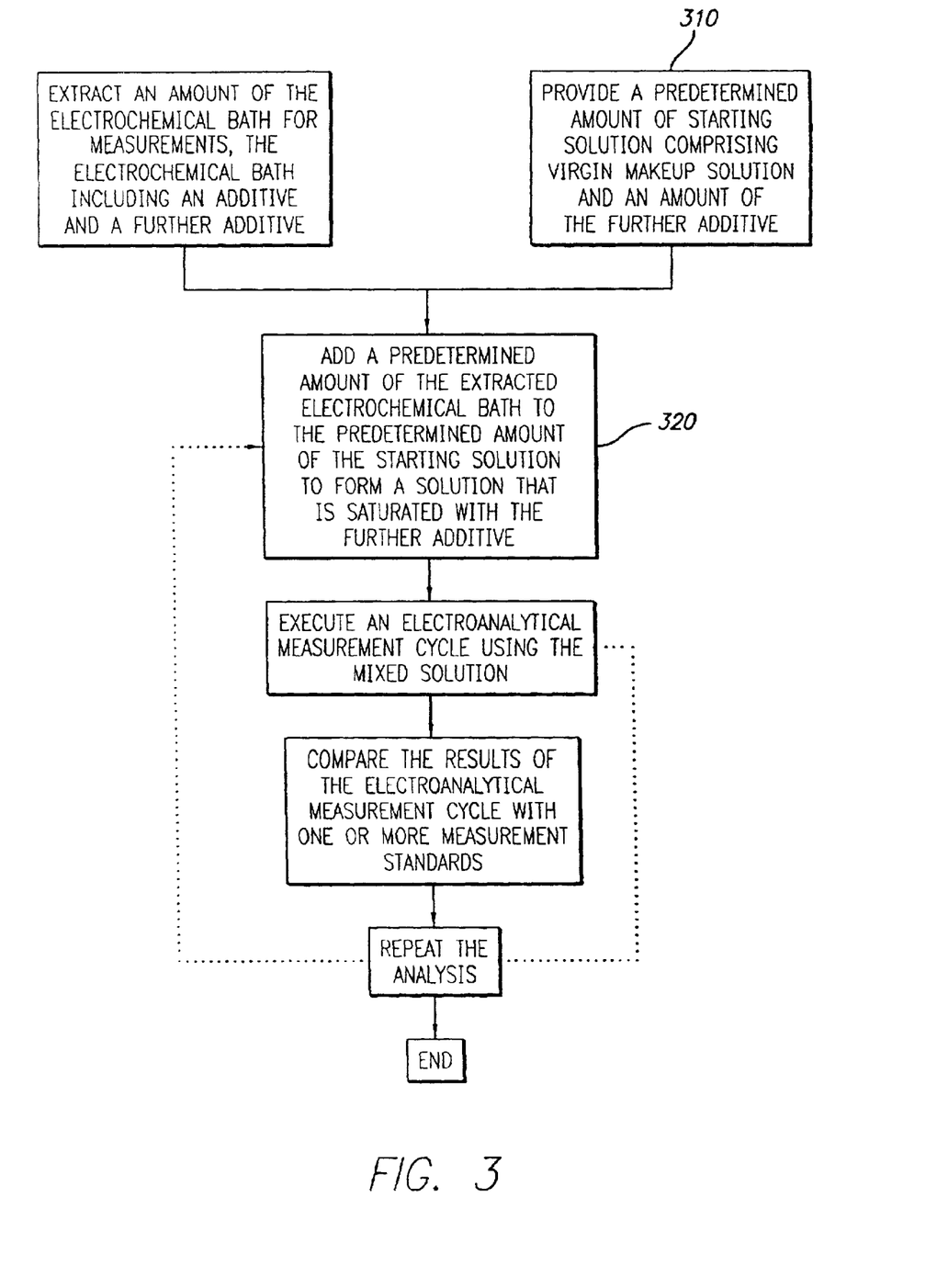
FIG. 3 is a flowchart illustrating a further process sequence used to analyze an electrolytic bath in accordance with a further embodiment of the present invention.

Generally, additive/constituent Y will have an impact on any electroanalytical measurements that are taken to determine the quantity of additive X that is present in the electrochemical bath. Additive/constituent Y may be comprised of one or more different chemicals that are purposely added to the electrochemical bath and/or are bath byproducts. In order to negate the effect that additive/constituent Y has on subsequent electroanalytical measurements involving both the electrochemical bath sample and the starting solution, the starting solution is chosen so that it is comprised of virgin makeup solution that is saturated with the additive/constituent Y. Alternatively, or in addition, the amount of additive/constituent Y present in the starting solution maybe chosen so that the total amount of additive/constituent Y in a mixed solution that includes a predetermined amount of the starting solution and a predetermined amount of the electrochemical bath renders the effect of additive/constituent Y negligible. For example, the amount of additive/constituent Y present in the starting solution plus an empirically, or otherwise, determined amount of additive/constituent Y in the electrochemical bath renders a mixed solution that is saturated with additive/constituent Y. An example of a process employing this latter method of insuring saturation of the additive/constituent is illustrated at steps 310 through 320 of FIG. 3.

At step 220, a predetermined amount of the extracted electrochemical bath is added to a predetermined amount of the starting solution. An electroanalytical measurement cycle is executed at step 225 on the mixed solution resulting from step 220. In accordance with one embodiment of the illustrated method, the electroanalytical measurement cycle may comprise a voltammetric technique such as CVS and/or CPVS. The result of the electroanalytical measurement cycle is then compared with one or more measurement standards at step 230. For example, the result of the electroanalytical measurement cycle may be compared to data representing a graph of known standard solutions that have been subject to such an electroanalytical measurement cycle. Alternatively, or in addition, the result of the electroanalytical measurement cycle may be used, either alone or with other electroanalytical measurement cycle results, in a mathematical calculation. This mathematical calculation, in turn, may be used alone, as the basis for comparison with known standard values, or in other mathematical calculations to determine the amount of additive/constituent X in the extracted bath sample or to determine the amount of a particular additive/constituent that is to be added by the corresponding dosing system.

In accordance with one embodiment of this method, a calibration curve is derived using a standardized solution that is saturated with both additive/constituent X and additive/constituent Y. This is done so that the same volumetric change occurs independent of whether the plating bath or the standard solution is added. As such, the volumetric change does not have a significant effect on the determination of the amount of the target constituent/additive that is present in the electrochemical bath.

Figure 4:
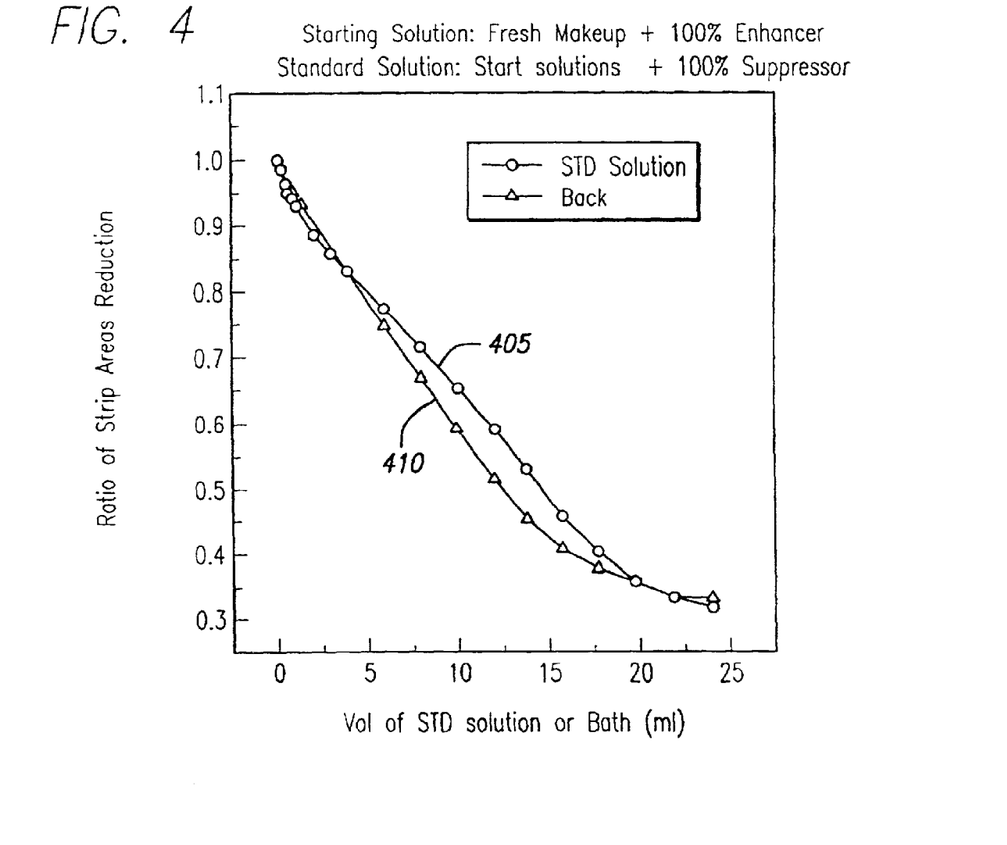
FIG. 4 is a graph illustrating experimental results obtained using a process sequence derived from the flowchart of FIGS. 2 and 3.

FIG. 4 is a graph illustrating the results obtained when additive/constituent X is an electroplating suppressor, additive/constituent Y is an electroplating enhancer and CVS is used as the electroanalytical technique. As shown, the ratio of strip areas reduction is plotted along the vertical axis while the volume of standard solution/electroplating bath is plotted along the horizontal axis. Curve 405 represents the results obtained with the standard solution while curve 410 represents the results obtained using the extracted electroplating bath sample. In accordance with one manner of implementing the methods shown in FIGS. 2 and 3, the electroanalytical measurement cycle maybe conducted in the manner set forth in U.S. Ser. No. 09/387,084, entitled "Methods and Apparatus for Controlling and/or Measuring Additive Concentration in an Electroplating Bath", filed Aug. 31, 1999.

Further electroanalytical measurements may be taken, if desired, as shown at step 235. For example, an electroanalytical measurement cycle, such as at 225, may be executed on a further predetermined amount of the extracted electrochemical bath and/or the starting solution. Such a process is exemplified by return line 240. Alternatively, or in addition, a further electroanalytical measurement cycle maybe executed on the same mixed solution. This option is illustrated at return line 245. It should be noted, however, that the analysis may be terminated without further repetition.

The foregoing analysis techniques may be implemented in an electroanalysis unit that is integrated with a dosing system for use with electroplating tools that are used at microelectronic fabrication facilities. Most known systems, however, execute the dosing function using open-loop, predetermined models that replenish the electroplating bath constituents based on empirically determined data. Such systems may be suitable for certain electroplating processes, but become less viable as new device requirements impose more rigorous standards on the make-up of the electroplating bath.

Figure 5:
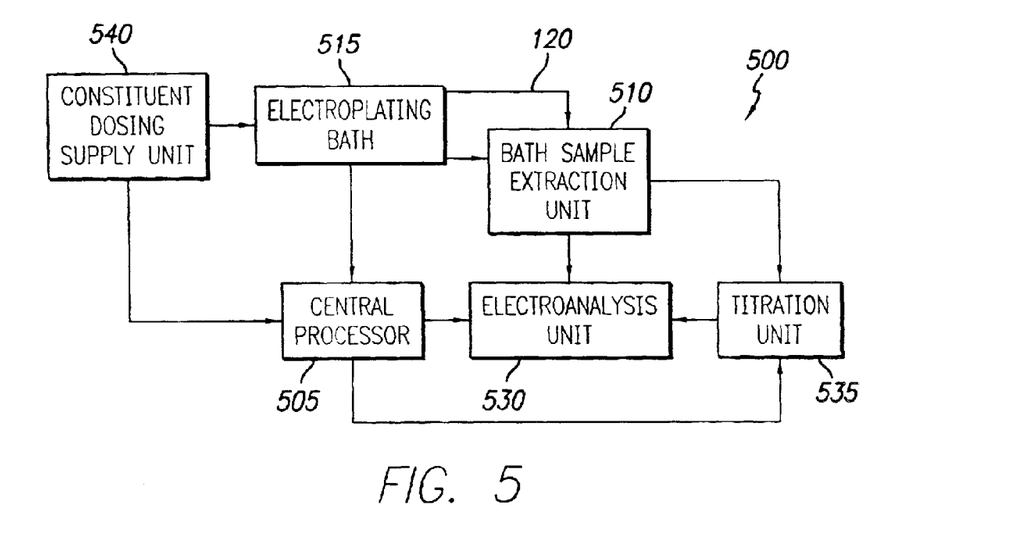
FIG. 5 is a schematic block diagram of one embodiment of an analysis and dosing system that that may be used to implement the processes of FIGS. 2 and 3.

More accurate control of the plating bath constituents maybe obtained using a dosing system that employs measurement feedback to ascertain the proper quantity of a bath additives that is to be dispensed. An exemplary feedback dosing system that may implement the foregoing process is illustrated in FIG. 5. As shown, the dosing system, shown generally at 500, includes a central processor 505 that is used to control the operations necessary to perform the following functions: 1) extract a sample of the electroplating bath that is to be analyzed; 2) execute an electroanalytical technique on the electroplating bath sample; 3) calculate the amount of the electroplating bath constituent present in the sample based on the results of the electroanalytical technique or otherwise derived a similarly useful indication of the effect of the constituent; and 4) use the resulting calculation to automatically control the supply of an amount of the constituent to replenish the electroplating bath, raising the constituent concentration to a predetermined level.

In order to execute such functions, the central processor 505 is connected to interact with and exchange information with a number of further units and systems. A bath sample extraction unit 510 is connected for control by the central processor 505. The bath sample extraction unit 510 is connected to receive electroplating solution along line 520 from the principal electroplating bath 515 in response to control signals/commands received from the central processor 105 along communication link 525. In response to such control signals/commands, the bath sample extraction unit 510 provides the bath sample to either an electroanalytical cell 40 of electroanalysis unit 530 or to a titration system 535.

Both the electroanalysis unit 530 and the titration system 535 are under the control of the central processor 505. The central processor 505 coordinates the activities of the electroanalysis unit 530 and titration system 535 to execute the desired electroanalytical technique. The central processor 105 then acquires the requisite data based on the electroanalytical technique to directly calculate or otherwise determine in a relative manner the concentration of the plating bath constituent. Based on this calculation/determination, the central processor 505 directs one or more constituent dosing supply units 540 to provide the necessary amount of the constituent (or amount of solution containing the constituent) to the electroplating bath 515, thus completing the feedback control process.

It will be recognized that the electroanalytical apparatus and techniques described above can be implemented in a manual, semi-automatic, or completely automatic manner. Dosing system 500 is provided as an illustrative, yet novel manner in which to implement one or more of the methods described above, as well as similar methods based on the teachings of the present application.

Numerous modifications may be made to the foregoing system without departing from the basic teachings thereof. Although the present invention has been described in substantial detail with reference to one or more specific embodiments, those of skill in the art to the will recognize that changes may be made thereto without departing from the scope and spirit of the invention as set forth in the appended claims.

What is claimed is:

1. A method for determining the concentration of an additive X of an electrochemical bath that includes at least one further component Y, the method comprising:

providing a predetermined amount of a starting solution, the starting solution comprising virgin makeup solution that is saturated with the further component Y;

extracting an amount of the electrochemical bath for measurement;

adding a predetermined amount of the extracted electrochemical bath to the predetermined amount of the starting solution to form a mixed solution;

executing at least one electroanalytical measurement cycle using the mixed solution; and comparing results of the electroanalytical measurement cycle with a known measurement standard.

2. The method of claim 1 wherein a plurality of electroanalytical measurement cycles are executed using the mixed solution and wherein the mixed solution used in the electroanalytical measurement cycles comprises mixed solutions having different amounts of the extracted electrochemical bath added thereto.

3. The method of claim 1 wherein the at least one electroanalytical measurement cycle comprises cyclic voltammetric stripping.

4. The method of claim 1 wherein the at least one electroanalytical measurement cycle comprises cyclic pulse voltammetric stripping.

5. The method of claim 1 wherein the known measurement standard is obtained prior to the comparing results of the electroanalytical measurement cycle by executing a plurality of electroanalytical measurement cycles using a standardized solution comprising virgin makeup solution that is saturated with the further component Y.

6. The method of claim 1 wherein the additive X is an electroplating suppressor.

7. The method of claim 1 wherein the component Y is an electroplating enhancer.

8. A method for determining the concentration of suppressor in an electroplating bath that also includes an electroplating enhancer, the method comprising:

providing a predetermined amount of a starting solution comprising virgin makeup solution that is saturated with the enhancer;

extracting an amount of the electroplating bath for measurement;

adding a predetermined amount of the extracted electroplating bath to the predetermined amount of the starting solution to form a mixed solution;

executing at least one electroanalytical measurement cycle using the mixed solution; and comparing results of the at least one electroanalytical measurement cycle with a known measurement curve.

9. The method of claim 8 wherein a plurality of electroanalytical measurement cycles are executed using the mixed solution and wherein the mixed solution used in the electroanalytical measurement cycles comprises mixed solutions having different amounts of the extracted electroplating bath added thereto.

10. The method of claim 8 wherein the at least one electroanalytical measurement cycle comprises cyclic voltammetric stripping.

11. The method of claim 8 wherein the at least one electroanalytical measurement cycle comprises cyclic pulse voltammetric stripping.

12. The method of claim 8 wherein the known measurement curve is obtained prior to the comparing results of the electroanalytical measurement cycle by executing a plurality of electroanalytical measurement cycles using a standardized solution comprising virgin makeup solution that is saturated with the enhancer.

13. A method for determining the concentration of an additive X of an electrochemical bath that includes at least one further component Y, the method comprising:

providing a predetermined amount of a starting solution, the starting solution comprising virgin makeup solution that includes a predetermined amount of the further component Y;

extracting an amount of the electrochemical bath for measurement;

adding a predetermined amount of the starting solution to form a mixed solution, the mixed solution being saturated with the at least one further component Y;

executing at least one electroanalytical measurement cycle using the mixed solution; and comparing results of the electroanalytical measurement cycle with a known measurement standard.

14. A method for determining the amount of an electrochemical bath additive that is to be automatically added to an electrochemical bath by a dosing system, the amount of the electrochemical bath additive that is to be added being dependent on a measurable value related to an amount of a component X in the electrochemical bath, the electrochemical bath also including at least one further component Y, the method comprising:

providing a predetermined amount of a starting solution, the starting solution comprising virgin makeup solution that is saturated with the further component Y;

automatically extracting an amount of the electrochemical bath for measurement;

automatically adding a predetermined amount of the extracted electrochemical bath to the predetermined amount of the starting solution to form a mixed solution;

automatically executing at least one electroanalytical measurement cycle using the mixed solution; and automatically using the results of the electroanalytical measurement cycle to determine the amount of additive that is to be dispensed by the dosing system.

15. The method of claim 14 wherein the electroanalytical measurement cycle comprises cyclic voltammetric stripping.

16. The method of claim 14 wherein the electroanalytical measurement cycle comprises cyclic pulse voltammetric stripping.

17. An automated chemical management system comprising:

a bath extractor connected to extract an amount of an electrochemical bath from an electrochemical processing unit, the bath extractor being adapted to extract an electrochemical bath that is comprised of a first bath additive, the amount of which is to be determined by the automated chemical management system, and a second bath additive, an electroanalytical measurement system including a container in which electroanalytical measurements are conducted, the container being adapted to hold an amount of virgin makeup solution that is saturated with the second bath additive, a programmable control system connected to control the bath extractor and the electroanalytical measurement system, the programmable control system being programmed to direct the bath extractor and electroanalytical measurement system for execution of a series of operations to determine the amount of the first bath additive in the electrochemical bath that has been extracted from the electrochemical processing unit, the operations comprising extracting an amount of the electrochemical bath from the electrochemical processing unit for measurement of the amount of the first bath additive therein, dispensing an amount of a virgin makeup solution that is saturated with the second bath additive into the container to form a mixed bath, executing at least one electroanalytical measurement cycle using the mixed bath, determining the amount of the first bath additive in the extracted electroplating bath using one or more measurements obtained in the at least one electroanalytical measurement cycle using the mixed bath.

18. The automated chemical management system of claim 17 wherein the first bath additive is an electroplating suppressor in the second bath additive is an electroplating enhancer.

19. The automated chemical management system of claim 17 wherein the electroanalytical measurement system executes cyclic voltammetric stripping.

20. The automated chemical management system of claim 17 wherein the electroanalytical measurement system executes cyclic pulse voltammetric stripping.

21. The automated chemical management system of claim 17 wherein the programmable control system determines the amount of the first additive by comparing one or more measurements obtained during the at least one electroanalytical measurement cycle to one or more measurements obtained using a standardized solution, the standardized solution comprising virgin makeup solution that is saturated with the second bath additive.

22. The automated chemical management system of claim 17 and further comprising a chemical dosing system connected to dispense an amount of the first bath additive based on the amount of the first bath additive in the extracted electroplating bath as determined by the programmable control system.

23. An automated chemical management system comprising:

a means for extracting an amount of an electrochemical bath from an electrochemical processing unit, the means for extracting being adapted to extract an electrochemical bath that is comprised of a first bath additive, the amount of which is to be determined by the automated chemical management system, and a second bath additive, an electroanalytical measurement system comprising a means for conducting electroanalytical measurements and for holding an amount of virgin makeup solution that is saturated with the second bath additive, and a control system including a means for controlling the means for extracting and the electroanalytical measurement system to facilitate the execution of a series of operations to determine the amount of the first bath additive in the electrochemical bath that has been extracted from the electrochemical processing unit, wherein the operations comprise:

extracting an amount of the electrochemical bath from the electrochemical processing unit for measurement of the amount of the first bath additive therein, dispensing an amount of a virgin makeup solution that is saturated with the second bath additive into the means for conducting so as to form a mixed bath, executing at least one electroanalytical measurement cycle using the mixed bath, and determining the amount of the first bath additive in the extracted electroplating bath using one or more measurements obtained in the at least one electroanalytical measurement cycle using the mixed bath.

24. A chemical management system for measuring a first bath additive in a sample containing at least the first bath additive and a second bath additive, comprising:

an electroanalytical measurement system in which electroanalytical measurements are conducted, the electroanalytical measurement system being adapted to hold the sample and an amount of virgin makeup solution that is saturated with the second bath additive, and a control system configured to execute a series of operations to determine the amount of the first bath additive in the sample when the sample and the virgin makeup solution are combined within the electroanalytical measurement system to form a mixed bath, the operations comprising obtaining at least one electroanalytical measurement using the mixed bath, and determining the amount of the first bath additive in the sample using the at least one electroanalytical measurement obtained using the mixed bath.

25. A method for determining the concentration of an additive X in a sample that includes at least the additive X and a further component Y, the method comprising the steps:

(a) providing a starting solution, the starting solution comprising virgin makeup solution that is saturated with the further component Y;

(b) adding the sample to the starting solution to form a mixed solution;

(c) executing at least one electroanalytical measurement using the mixed solution; and (d) comparing results of the at least one electroanalytical measurement with a known measurement standard.

26. A chemical management system for measuring a first bath additive in a sample containing at least the first bath additive and a second bath additive, comprising:

a measurement system including means for holding the sample and an amount of virgin makeup solution that is saturated with the second bath additive and for conducting electroanalytical measurements, and a control system including:

means for executing a series of operations to determine the amount of the first bath additive in the sample when the sample and the virgin makeup solution are combined within the means for holding to form a mixed bath; and means for conducting electroanalytical measurements, wherein the series of operations comprise:

obtaining at least one electroanalytical measurement using the mixed bath; and determining the amount of the first bath additive in the sample using the at least one electroanalytical measurement obtained using the mixed bath.

* * * * *